United States Patent
Sablone (10) Patent No.: US 9,468,562 B2
(45) Date of Patent: Oct. 18, 2016

(54) METHOD FOR PRODUCING SANITARY ARTICLES WEARABLE AS PANTS PROVIDED WITH SIDE PANELS, AND CORRESPONDING ARTICLE

(75) Inventor: Gabriele Sablone, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 581 days.

(21) Appl. No.: 14/007,267

(22) PCT Filed: Mar. 7, 2012

(86) PCT No.: PCT/IB2012/051063
§ 371 (c)(1),
(2), (4) Date: Sep. 26, 2013

(87) PCT Pub. No.: WO2012/131509
PCT Pub. Date: Oct. 4, 2012

(65) Prior Publication Data
US 2014/0018222 A1 Jan. 16, 2014

(30) Foreign Application Priority Data
Mar. 31, 2011 (IT) .............................. TO2011A0287

(51) Int. Cl.
*A61F 13/15* (2006.01)
*A61F 13/494* (2006.01)

(52) U.S. Cl.
CPC ......... *A61F 13/15* (2013.01); *A61F 13/15756* (2013.01); *A61F 13/4942* (2013.01); *A61F 13/49413* (2013.01)

(58) Field of Classification Search
CPC ............. A61F 13/15; A61F 13/15756; A61F 13/49413; A61F 13/4942
See application file for complete search history.

(56) References Cited

U.S. PATENT DOCUMENTS 5,399,219 A   3/1995 Roessler et al.
5,476,458 A * 12/1995 Glaug ............... A61F 13/15203
                                                          604/358

(Continued)

FOREIGN PATENT DOCUMENTS

EP          1 941 853 A1    7/2008

OTHER PUBLICATIONS

Jun. 12, 2012 International Search Report for Application No. PCT/IB2012/051063 (3 pages).

*Primary Examiner* — Philip Tucker
*Assistant Examiner* — Christopher C Caillouet
(74) *Attorney, Agent, or Firm* — Popovich, Wiles & O'Connell, P.A.

(57) ABSTRACT

A method for producing sanitary articles (10) wearable as pants, provided with at least one pair of side panels (16) designed to connect the end parts of the article around the waist of the user envisages providing a web of laminar material (31) for the aforesaid side panels (16) and subjecting said web of laminar material (31) to segmentation (90) by cutting the web with cuts (91, 91') so as to obtain a chain of said side panels (16). Two webs of laminar material are provided for the lateral containment sheets (22) of the topsheet (13), and each side panel (16) is connected (110) by welding (45) to the corresponding lateral containment sheet (22) at its own proximal edge (160). Once the two lateral containment sheets (22), with each of the containment sheets (22) provided with the respective side panels (16), have been reversed and spaced apart (140), and once the two lateral containment sheets (22) have been aligned (150) by aligning pairs of side panels (16) transversely with respect to one another, a web of hydrophilic laminar material (21) is provided, and said web (21), with the two containment sheets (22), is joined to each of the containment sheets (22) provided with the corresponding side panels (16) aligned transversely with respect to one another.

10 Claims, 5 Drawing Sheets

(56) References Cited

U.S. PATENT DOCUMENTS 6,264,784 B1  7/2001  Menard et al.

2005/0256495 A1* 11/2005 Schlinz ............ A61F 13/15756
604/385.201

* cited by examiner

METHOD FOR PRODUCING SANITARY ARTICLES WEARABLE AS PANTS PROVIDED WITH SIDE PANELS, AND CORRESPONDING ARTICLE

TECHNICAL FIELD

The present description relates in general to the production of sanitary articles of the type that can be worn like pants.

Said term is used herein in its widest meaning, such as to include, for example, babies' diapers (nappies) of the pre-closed type (i.e., the ones commonly known as "training pants") and products for incontinence.

TECHNOLOGICAL BACKGROUND

Figure 1:
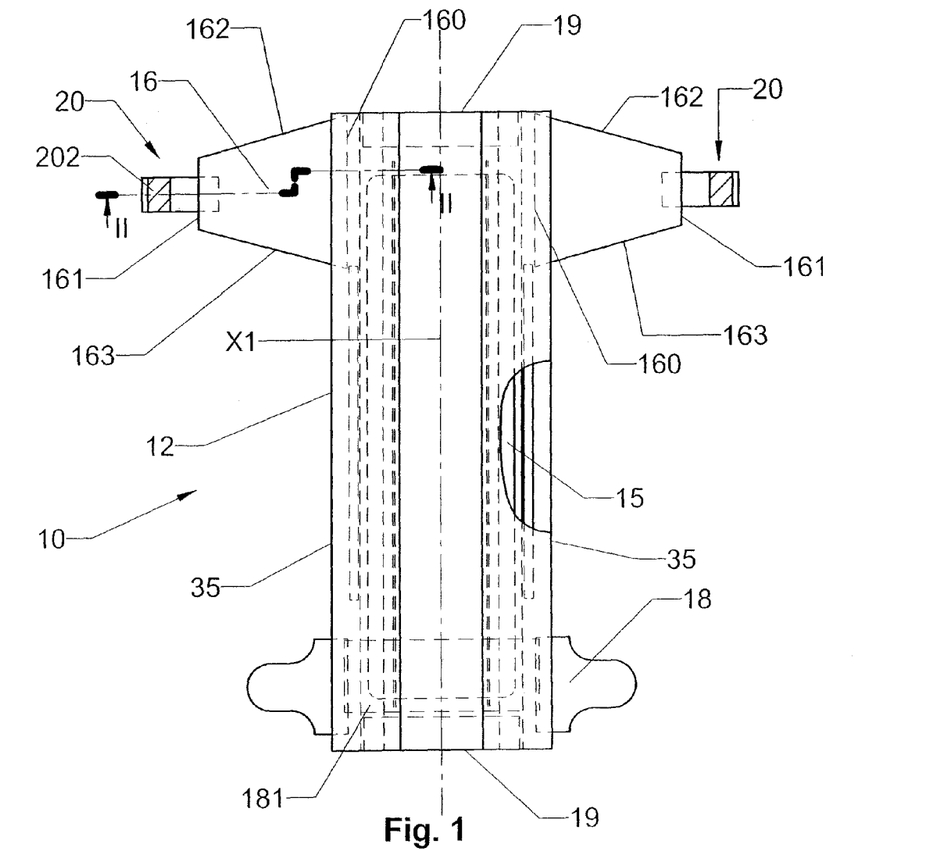
FIG. 1 is a general top plan view of a sanitary article that can be worn like pants provided with side panels of the type described herein, represented in a splayed-out condition.

In the sector of sanitary articles wearable as pants (nappies for small children and newborns, diapers for incontinent persons, etc.), there has continued to assert itself to an increasing extent the general structure represented, by way of example, in FIG. 1, where an article of the type considered herein is represented in the splayed-out condition and with the surface that is in contact with the body of the user facing the observer.

An article 10 of this sort is constituted by a central body or "chassis" 12 that is to be set according to a general concave configuration around the groin area of the user. The body 12 includes an absorbent core 15 sandwiched between a topsheet 13, which may be partially or totally permeable to body liquids, and an impermeable backsheet 14.

To enable the article 10 to be worn like pants, closing it around the waistline of the user, side panels are present, i.e., laminar elements, namely, a rear laminar element 16 and a front laminar element 18, that can be connected in a closed condition around the waistline of the user by means of closing elements 20 set at the distal margins 161 of the side panels 16.

The side panels 16 are particularly complex and sophisticated closing systems. To meet the needs of use in a complete way, the side panel must both perform functions of a structural nature (enabling closing of the sanitary article around the legs and the waist region of the user, ensuring the maximum degree of wearability) and enable transpiration of the skin preventing undesirable phenomena of maceration of the user's skin due to local stagnation of the moisture.

Examples of structures of sanitary articles inspired by said arrangement are illustrated, for example, in the documents Nos. EP-A-0 669 121 or WO-A-95/17871.

To guarantee a good wearability of the sanitary product, the rear panel 16 must have a trapezial shape, with the internal edge 163 shaped so as to form an obtuse angle with the longitudinal axis X1 of the diaper. Conversely, the external edge 162 can be perpendicular to the aforesaid axis X1 or, as in the case illustrated herein, can also present an obtuse angle of the same amplitude, in absolute value, but with a direction contrary to the one formed by the aforesaid internal edge 163.

Examples of methods for producing absorbent products with side panels with the two edges, the outer one 162 and the inner one 163, that do not form an angle of the same amplitude with the axis X1 of the diaper, i.e., with the side panels that have an asymmetrical conformation, are illustrated in the documents No. EP-A-1 941 853 and Italian Patent Application No. CH10A000015.

The methods described in the aforesaid documents present, however, problems; namely: for the method described in Italian Patent Application No. CH10A000015 there is an important limitation linked to the cost of the absorbent product; in fact, the aforesaid method teaches to provide a profiling of the panel by making on the latter a shaped cut, with corresponding removal and discarding of raw material, which for these particular applications is very costly.

As regards the document No. EP-A-1 941 853, which teaches to provide a diaper with side panels with asymmetrical shaping without generation of waste material, the drawback of the solution is to be sought in the complexity of the equipment, which hence reflects in an excessive cost of the production line and in the need to have available skilled staff for managing and running the production plant.

In general, the inventor has noted that, having to cut out shaped elements from a strip or web of raw material, it is possible to select profiles of the elements in question such as to create a situation of geometrical complementarity of the outlines of said elements, i.e., such as to have the two angles formed by the side edges of the panels with the longitudinal axis of the absorbent product of the same amplitude. For example, from FR-A-2 644 694 a solution is known in which, having to provide winged-type sanitary pads for women the starting point is a web that is cut lengthwise according to an approximately sinusoidal cutting path. The two half-strips thus obtained are turned over and connected back to back so as to obtain a weblike material with the desired profiling without giving rise to waste material.

An intrinsic drawback of this type of solution lies, however, in the fact that to the side panels thus formed it is not possible to associate projecting closing elements, unless by applying them to the individual panels after the latter have been cut. The inventor has found that the operation just suggested proves to be of an extreme complexity; consequently, a solution of this type limits considerably the possibility of choice of closing elements to just non-projecting elements applied directly on the side panels.

OBJECT AND SUMMARY

The prior art referred to above leaves open two basic problems: the first regards providing side panels for sanitary articles that can be produced without generating waste of the material with which they are made and that are suited to being equipped with projecting closing elements such as, for example, adhesive labels or labels provided with mechanical-engagement systems; the second regards applying the aforesaid side panels on the individual absorbent products with an inexpensive and simple procedure, i.e., one that can be managed and implemented easily.

According to the present invention, the above object is achieved thanks to a method having the characteristics recalled in claim 1. Advantageous developments of the invention form the subject of the dependent claims. The invention also regards a corresponding sanitary article obtained with the present method.

The claims form an integral part of the technical teaching provided herein in relation to the invention.

BRIEF DESCRIPTION OF THE FIGURES

The invention will now be described, purely by way of non-limiting example, with reference to the annexed plates of drawings, wherein.

DETAILED DESCRIPTION

In the ensuing description various specific details are illustrated aimed at an in-depth understanding of embodiments. The embodiments may be provided without one or more of the specific details, or with other methods, components, materials, etc. In other cases, known structures, materials, or operations are not illustrated or described in detail so that the various aspects of the embodiments will not be obscured.

The reference to "an embodiment" or "one embodiment" in the framework of this description is intended to indicate that a particular configuration, structure, or characteristic described in relation to the embodiment is comprised in at least one embodiment. Hence, phrases such as "in an embodiment" or "in one embodiment" that may be present in various points of this description do not necessarily refer to one and the same embodiment. In addition, particular conformations, structures, or characteristics can be combined in any adequate way in one or more embodiments.

The references used herein are merely for convenience and hence do not define the sphere of protection or the scope of the embodiments.

In FIG. 1 the reference number 10 designates as a whole a sanitary product that can be worn like pants, here illustrated in a plane splayed-out condition. In its basic terms, FIG. 1 has already been described previously so that, except for what will be explicitly said in what follows, parts and elements that are identical or equivalent to parts or elements already described in relation to FIG. 1 will not be described any further herein.

In the example illustrated here, the article in question (diapers for babies or diapers for incontinent adults) is of a conventional type that is to be sold open and closed like pants after being set on the body of the user. Various embodiments can in any case be applied also to the articles commonly referred to as "training pants", that are to be sold already closed in the pant configuration and be worn by the user.

As has already been said, in basic terms, the product 10 is made up of a central structure 12 (or crotch portion) that is to be applied on the body of the user, which bestows a general concave or U conformation that wraps round the area of the groin.

In certain embodiments, the body or chassis 12 can have a structure in which there may be usually recognized (in addition to various other accessory elements):

a top layer or "topsheet" 13 that is to face the body of the user;

a bottom layer or "backsheet" 14 impermeable to body liquids, that is to face outwards, i.e., in contact with the garments worn by the user; and an absorbent core 15, set between the topsheet 13 and the backsheet 14.

Side panels are then present, designated by the references 16, which extend from the central body 12 and enable (for example via adhesive closing systems 20 or Velcro microhook systems) closing of the article along the waistline as worn by the user.

In the example of embodiment described, the topsheet 13 is a sheet material obtained by putting together three materials, namely, the central sheet 21 permeable to body liquids, and the two lateral containment sheets 22 or "cuffs", which, in turn, are made of water-repellent material, so as to be able to contain any possible lateral leakages of exudate. To improve the effect of containment of liquids performed by the sheets 22, the latter can be equipped with elastic elements 23, which, applied on the sheet in the splayed-out configuration, at the moment when the absorbent product is invited to assume the classic concave conformation for being worn, contribute to causing the internal edges 24 of the sheets 22 to be raised. The materials for producing the sheets necessary for the production of the topsheet can be chosen starting from natural or synthetic fibres, such as, for example, polyester or polypropylene, and can even be a mixture of synthetic and natural fibres. An adequate material for producing the liquid-permeable central element 21 of the topsheet 13 is a non-woven fabric of polypropylene fibres with a substance of 25 g/m$^2$ obtained with Spunbond technology, rendered hydrophilic by means of a surface treatment with surfactant products such as Ahcovel N-62 manufactured by Hodgson Textile Chemicals of Mount Holly, N.C. U.S.A. and/or Glucopan 220UP manufactured by Henkel Corporation of Amber, Pa. U.S.A.

In certain embodiments, the side sheets 22 may be made with a 25-g/m$^2$ multilayer laminate of non-woven fabric of polypropylene fibres constituted by a lamina produced with Spunbond technology, a subsequent sheet produced with Meltblown technology, and finally a further Spunbond layer.

The side panels 16 can be made of materials produced according to the criteria described more fully in the documents Nos. WO-A-01/91666 and WO-A-01/92013, this also as regards the possibility of bestowing upon the panels 16 characteristics of "breathability", with the formation of openings that enable the passage of vapour and contribute to keeping the skin of the user dry.

The side panels can be present on both of the ends (front and rear ends) of the central body 12. This is usually the case of articles of the training-pant type, where the distal margins of the various panels are welded together to bestow on the article, as sold, the closed conformation.

It is emphasized that the terms "front" and "rear" are used herein only for distinguishing the two ends from one another and consequently do not have any specific importance as regards the modalities with which the product is finally worn.

The example of embodiment illustrated herein regards the case (more frequent in the products sold "open") in which the side panels 16 provided with closing systems 20 are present at the rear end of the central body 12, whilst two tabs 18 project laterally from the front end of the central body 12 bestowing upon the article 10 (viewed ideally in an open and splayed-out condition, as represented in FIG. 1) the typical hourglass conformation, accentuated by the fact that the side panels 16 have a generally trapezial shape.

The representation of FIG. 1 is of a schematic nature and is intended to highlight that the solution described herein can be applied to a wide variety of possible types of embodiment of the article 10.

For a more detailed illustration of further characteristics of the article 10 (for example, as regards the presence of edges that are shaped and delineate the contour of the openings for the legs of the user and again as regards the presence of the so-called elasticized "cuffs" or sides 22 set along the sides of the absorbent core 15 with a function of lateral containment of the body fluids) reference may be made to the ample literature existing on the subject: this applies also in relation to the possible choice of the materials making up the various parts of the article 10.

Figure 2:
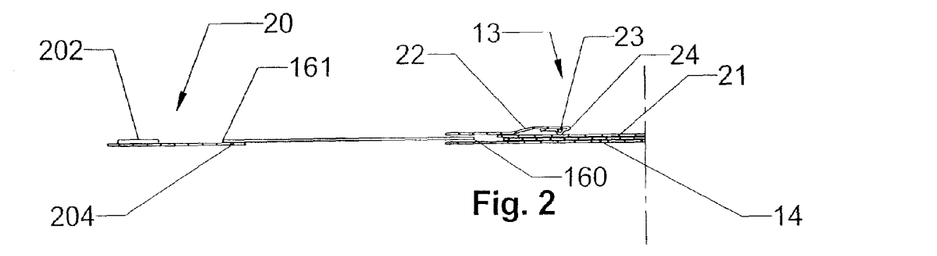
FIG. 2 is a cross-sectional view according to the line II-II of FIG. 1.

As may be appreciated better in the cross-sectional view of FIG. 2, for the connection of the side panels 16 the solution described herein envisages that the proximal margins 160 are connected with the modalities of connection that will be described in the sequel of the present document, and welding to the body or chassis 12 of the article 10 is obtained either by sandwiching the individual side panels 16 between the topsheet 13 and the backsheet 14 of the body of the article 12 or by positioning them directly on the topsheet 13 on the surface that faces the body of the user.

Figure 3:
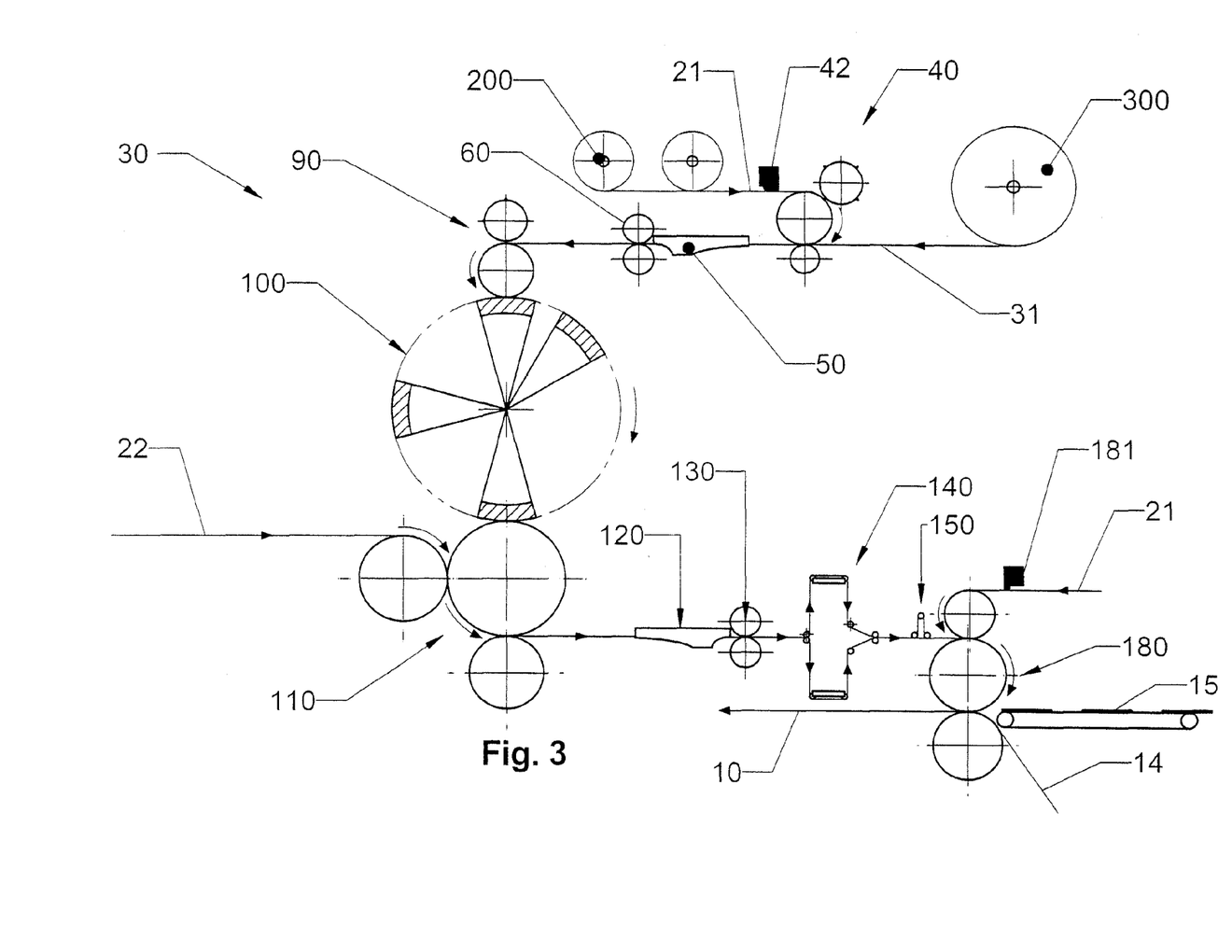
FIG. 3 is a general view in side elevation of a plant that can be used for the production and application of the side panels operating according to one embodiment.

In certain embodiments, a possible method of production of sanitary products, such as for example babies' diapers, provided with side panels 16 of the type described herein, may correspond to the scheme of FIG. 3.

The web of material 31 necessary for providing the side panels 16 is supplied to the production line from a roll 300 by means of a unit for feeding web material in itself known.

Figures 4, 5:
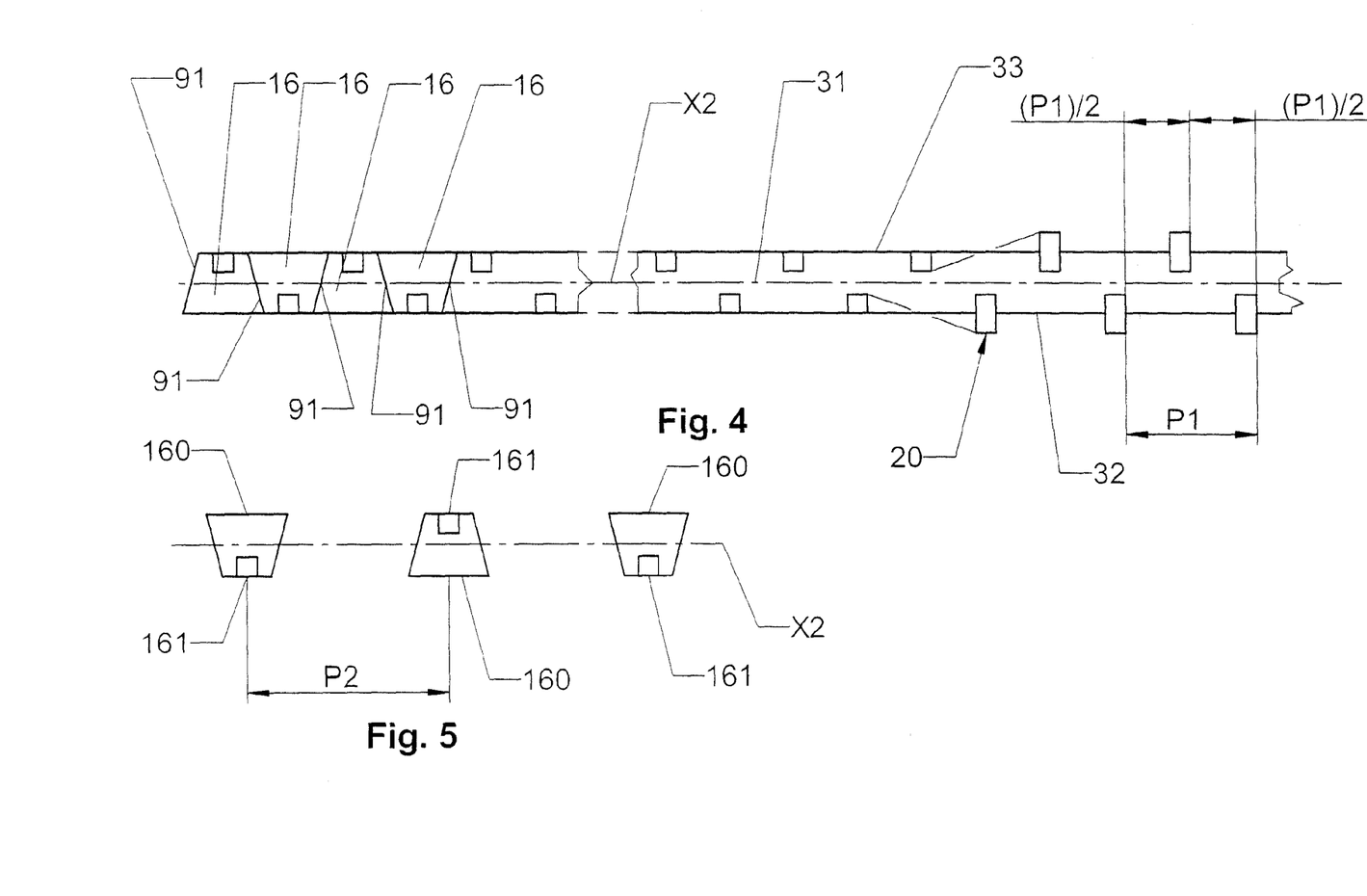
FIGS. 4 to 7 illustrate successive steps of embodiments of a method for production and application of side panels.

The web 31 traverses an applying station 40, which cuts, spaces, and deposits thereon a plurality of closing elements 20 in the form of strips of multilayer material, which, as may be appreciated from FIG. 4, are applied on both of the side edges 32 and 33 of the sheet 31 staggered with respect to one another; i.e., in other words, each closing element 20 applied on one edge is located in a position equidistant from the other two closing elements 20 that precede it and follow it but that are applied on the opposite edge. In other words, we can say that on each edge, the strips of material 20 are attached so as to have a constant spacing or pitch P1 between them, whilst they maintain a distance equal to half the pitch P1 with respect to the two closest strips of material 20 set, however, on the opposite edge.

As regards the operations of cutting, spacing (cut & slip), and application of elements coming from web material, which must be located at fixed distances from one another on a material that is also in sheet form, with reference alone to the patent documents filed in the name of the present applicant, it is possible to resort to a unit 40, the technical solution of which is described in EP-A-1 864 768.

The formations 20 are supplied from rolls of material 200, which are also wound off with a unit for feeding web material in itself known. The aforesaid materials can be tapes provided with adhesive or else sheets provided on which are strips having hook formations 202 that can co-operate with complementary materials with loop formations 181, such as to provide a closing of the hook-&-loop or "mechanical" type, which is very much appreciated by users owing to the possibility of opening and closing the system any number of times without jeopardizing the grip and owing to the fact that this type of closing is insensitive to possible contamination by emollient creams for the skin of the user and/or by body fluids. A hook material usable in the present context is available from the company Binder GmbH of Tuttlingen (Germany).

In the case where the use, by way of (non-limiting) example, on the two webs 21 of closing elements or labels 20 in the form of hook formations is considered, before the latter have been segmented in the station 40, it is necessary to spread a layer of glue 204 along the band of the marginal edge of each of the webs 21 that is in contact with the respective edge of the web 31. The adhesive is spread on the aforesaid webs with a unit for applying the adhesive 42 in itself known. After segmenting the web materials 21, generating the individual closing elements 20, the station 40 spaces them and applies them on the web 31 with the desired pitch P1, as is clearly visible in FIG. 4. Said labels 20 are applied on the edges of the sheet 31 so as to cause the portion of the web 20 provided with the hook material 202 to project outwards.

Said application pitch P1 is chosen as a function of the size of the product that is to be made and, consequently, as a function of the longitudinal dimensions of the individual panels 16.

Set downstream of the station 40 is a folding device 50, generally made with two tunnels with a helical conformation set at the outer sides of the web 31, which complete the operation of application of the closing systems by folding the formations 20 themselves according to a general V-shaped conformation so as to bring them to embrace the opposite faces of the web 31.

The connection of the formations 20 is then strengthened by an operation of pressing performed in a station 60 constituted by two counter-rotating rollers.

The pressing station 60 normally also has the function of station for feeding the web 31. The aforesaid unit dispenses to the equipment of the method present downstream the right amount of material according to the speed of the production line.

At output from the roller pressing unit 60 the web enters the shaped-cutting station 90 which is entrusted with the following functions:

cutting the web into the desired shape, which, in certain embodiments, can reproduce a profile shaped like an isosceles trapezium, so as to obtain a row of successive lengths, each of which provided with its own closing element 20 set at the centre of the minor base of the trapezium, so as to generate the side panels 16; and transferring the side panels 16 to the subsequent repitching unit 100, which spaces them and sends them on to the next application unit, as will be better appreciated in what follows.

The unit 90 performs a series of cuts 91 on the web 31 so as to obtain a sequence of panels 16, each of which is oriented specularly with respect to the panels closest thereto; namely, each panel 16 has closing systems 20 facing in an opposite direction with respect to the panel 16 that precedes it and to the panel 16 that follows it.

At this point, in the example of embodiment illustrated, the panels 16 are fed to a repitching unit 100 built according to criteria in themselves known. For example, limiting our attention to the patent documents filed in the name of the present applicant, as regards the repitching operation it is possible to resort to the solutions described in EP-A-1 179 495 and in EP-A-1 772 403. The aforesaid repitching unit 100 will be built in such a way as to vary the separation pitch between successive panels 16 bringing them to the pitch P2 necessary for the specific requirements of application on the respective sanitary articles, which in certain embodiments can be equal to half the length of the finished absorbent product.

Next, as may be appreciated more fully in the view of FIG. 3, the panels 16 are made to converge in the welding unit 110 together with the two sheets 22, which are the elements of the topsheet 13 that provide the elements for lateral containment of the exudate, better known as "cuffs". At inlet to the heat-welding unit 110 the panels 16 are laid on the two sheets 22 in such a way that the middle axis X2 of the individual panels 16 always coincides with the axis X3 of the pair of sheets 22.

As has already been said previously, the panels 16 meet up with the sheets 22 in a sequence such that each panel has a specular orientation with respect to the panel that precedes it and to the panel that follows it. Consequently, the edge of the panel that coincides with the major side of the isosceles trapezium, i.e., the marginal edge 160 of each panel 16, is located on one sheet, whilst the homologous proximal edges 160 of the panels that, respectively, precede it and follow it are located on the other sheet. Consequently, the welding unit 110 joins together each panel 16 along its own marginal edge 160 with the respective sheet 22 with the weld 45.

At the moment when the two sheets 22 are fed to the welding unit 110 they are already provided with the elastic elements 23 that concur to raising the containment sheets themselves, bestowing upon the absorbent product the characteristic concave configuration.

Figure 6:
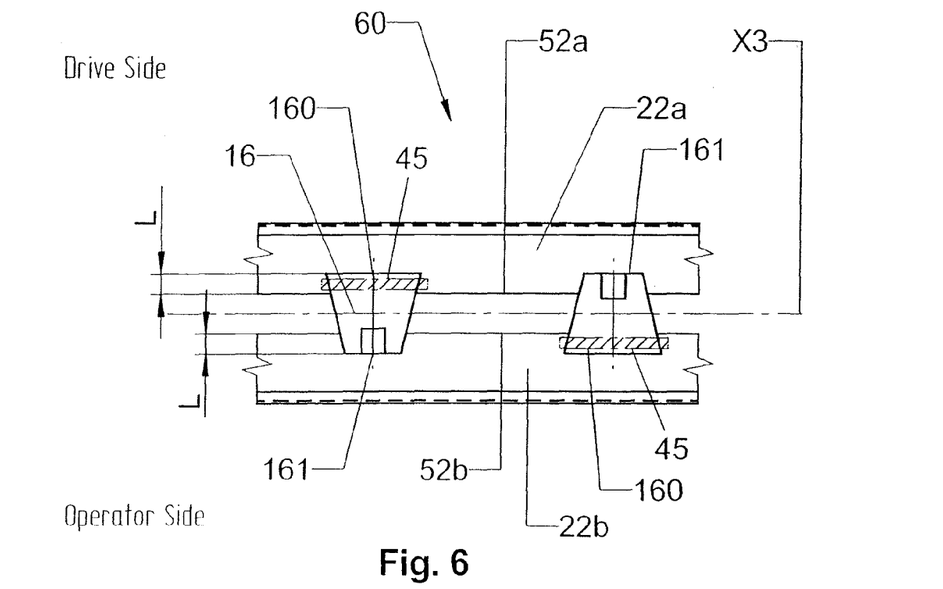

In certain embodiments, as may be appreciated more fully in the view of FIG. 6, the two sheets 22 can be fed to the welding unit 110 with the edges provided with the elastic elements 23 facing outwards.

The sheets 22a and 22b are fed to the welding unit 110 with a distance between their internal edges 52a and 52b such that the proximal and distal edges 160 and 161 of each panel 16 are superimposed on the aforesaid webs 22a and 22b by the same amount L.

The dimension L identifies the amount of material necessary for making a weld 45 that is reliable and presents adequate mechanical strength. By working with a thermo-mechanical or ultrasound welding unit it has emerged that, other parameters remaining the same, the best welding results are obtained by operating with overlap values L comprised between 5 and 25 mm, and in certain embodiments, with an overlap chosen between 10 and 20 mm. Certain embodiments can adopt the value of 15 mm as overlap value L.

In certain embodiments, the process hence presents an axial symmetry. In fact, the axes X1, X2 and X3, i.e., the longitudinal axes of the absorbent product 10, of the panels 16, and of the two sheets 22, coincide. Consequently, by depositing the panels 16 on the sheets 22, the distal edges 161 and proximal edges 160 of the individual panels overlap by the same amount L both of the internal edges 52a and 52b of the sheets 22.

In certain embodiments, the weld 45 can be performed just on the marginal edges 160 of the panels 16, i.e., on the edges of the panels without closing element 20. Consequently, the welding unit will once operate on the sheet 22a and then on the sheet 22b and so forth, always in an alternating way.

Examples of equipment suitable for performing welding of web materials are available in the patent literature (see, by way of example, EP-B 0 295 957 entitled "Dynamic mechanical bonding method and apparatus").

In certain embodiments, as may be appreciated more fully in the view of FIG. 3, at output from the welding unit 110 the material 60 made up of the two sheets 22 and of the plurality of panels 16 welded alternatively thereon, can be introduced in a folding unit 120 that turns each panel 16 over in a known way on the respective sheet 22 to which it belongs according to a general V-shaped conformation so as to bring said panels 16 to embrace the opposite faces of the respective sheets 22.

Examples of equipment suitable for making the fold of projecting elements are available in the patent literature (see, by way of example, U.S. Pat. No. 7,500,941 B2).

Immediately after the folding step, the material 60 is made to pass through the welding unit 130, which makes fixing spots 71 between the panels 16 and the respective sheets 22a and 22b to which they belong, so as to be able to perform in a convenient way the subsequent operations of reversal, spacing, and staggering of the aforesaid two sheets 22a and 22b. In other words, in the welding unit 130 a so-called "technical" weld is made, i.e., a weld that has only the function of simplifying and rendering more convenient and reliable the subsequent operations necessary for producing the sanitary product, but serves no purpose as regards the absorbent product. In fact, the welding spots 71 must be sufficiently strong as to withstand the stress of the production process but, at the same time, must be sufficiently weak as to break as soon as the user opens the diaper to wear it.

In certain embodiments, the operation of technical welding just described can be performed with any known means, such as, for example, thermo-mechanical or ultrasound welding, or by using adhesives, which in turn can be permanent, i.e., such as not to lose their characteristics with the passage of time, or provisional, i.e., such as to lose in part or completely their characteristics of adhesion as they dry.

In certain embodiments, on the sheets 22a and 22b there can be performed an operation of reversal and spacing of the sheets themselves. The aforesaid processes are performed by means of the equipment 140, which in the specific case may be made either with a series of idle rollers with axes that are skew with respect to the working surface of the main process, or with an equipment for aligning the edges of the sheet of the Symat 25 type, provided with sensors SE 22 and with a processor CDP-01-M produced and marketed by Fife GMBH, Fifestrasse 1, 65779 Kelkheim, Germany.

In certain embodiments, as may be better appreciated in the view of FIG. 6, the composite material 60 leaving the technical-welding unit 130 can be such that the elastic elements 23 face outwards, whilst the edges 52a and 52b of the sheets 22 face inwards, and again, the sheet 22a is positioned towards the inside of the process, or transmission side, of the production line, whilst the sheet 22b is arranged towards the outside of the process, or operator side. At output from of the reversal and spacing assembly 140 the composite material 60 will have assumed the following configuration 60': the sheets 22a and 22b will have reversed their position; i.e., the sheet 22a, which before was facing the transmission side now is faces the operator side, and obviously, the opposite applies to the sheet 22b. Moreover, the edges with the elastic elements 23 will be set facing towards the inside of the absorbent sanitary product, whereas the edges 52a and 52b will be set facing the outside of the diaper, thus becoming part of the distal edges 30 of the chassis 12.

Once again is it is emphasized that the terms "transmission side", "operator side" or inside and outside are here used only for distinguishing the two side ends and hence do not have a specific importance as regards the modes with which the product is finally obtained.

Figure 7:
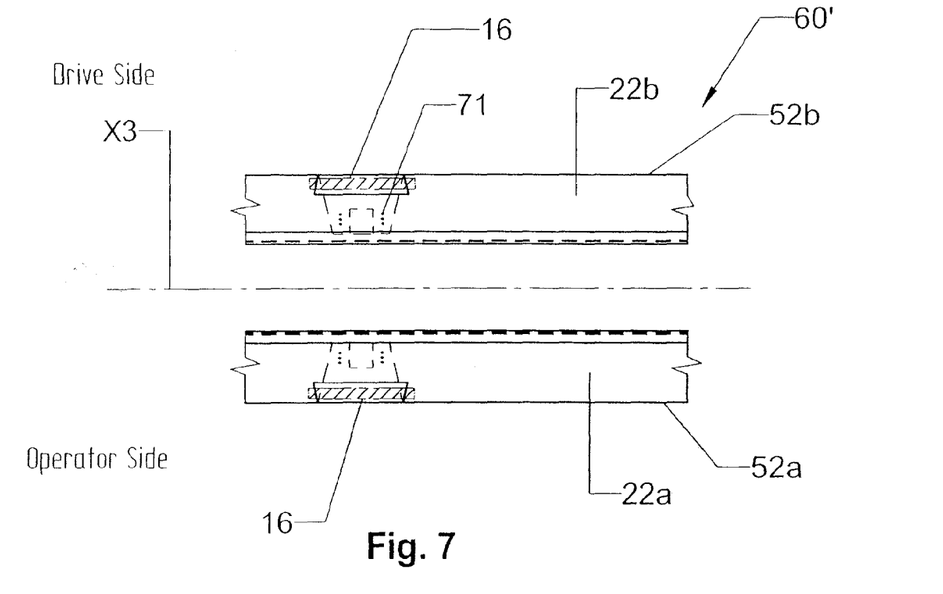

Immediately downstream of the assembly for reversal and spacing of the sheets 22 the operation of staggering of the sheets is carried out. In particular, in this step of the method the pairs of side panels 16 line up transversely, as represented in FIG. 7.

The aforesaid operation is conveniently completed with the equipment 150, which is merely a system of idle rollers that get the two sheets 22a and 22b to follow two paths of different length. Specifically, the two paths are made to differ with respect to one another by a length equal to P2 or to an integer multiple thereof.

Consequently, at output from the equipment 150 the composite material 60', i.e., the two sheets 22 with the side panels 16 welded, folded on themselves, and held stationary in their position by the technical welds 71, correctly staggered with respect to one another and at the desired centre-to-centre distance, is sent on to the coupling unit 180 where it is joined to the sheet material 21, which, as we have already said, is the third material constituting the topsheet 13, and in particular is the central component permeable to liquids.

In certain embodiments, coupling of the sheet 21 with the two sheets 22 can be obtained by gluing thanks to the strips of adhesive spread on the sheet 21 by the unit for applying the glue 181. Consequently, in this way, the composite sheet 13 or topsheet that comes into contact with the body of the user is formed.

In the same unit, or in a process unit with characteristics that are similar and in themselves known, the topsheet 13 already provided with panels 16 will be joined to all the other elements constituting the absorbent product.

It will be appreciated that, even though it has been developed on the basis of the need to treat shaped panels with the shape of an isosceles trapezium, set in the rear part of the absorbent sanitary product, the method illustrated can be used also to obtain a diaper with the front panels made with the same sheet as the one with which the rear panels are obtained.

Figure 8:
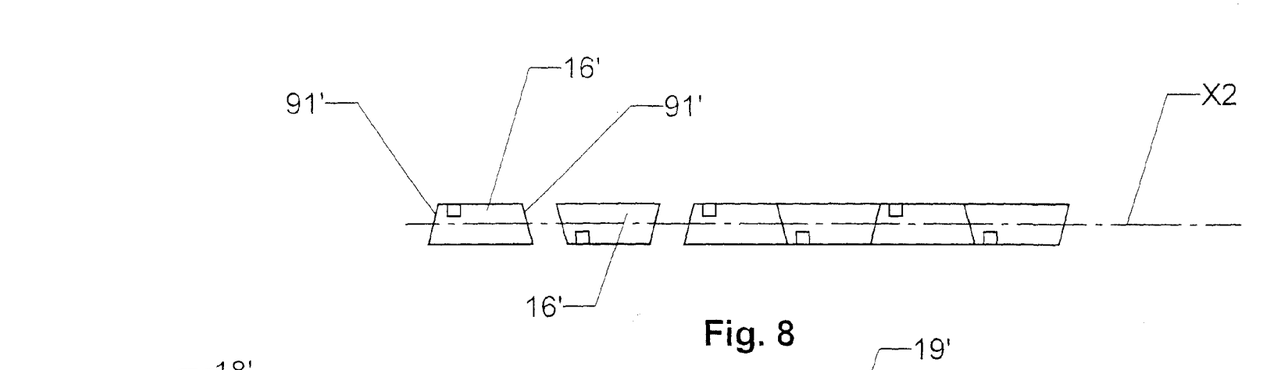
FIGS. 8 and 9 illustrate an example of method and corresponding sanitary article according to one embodiment.
Figure 9:
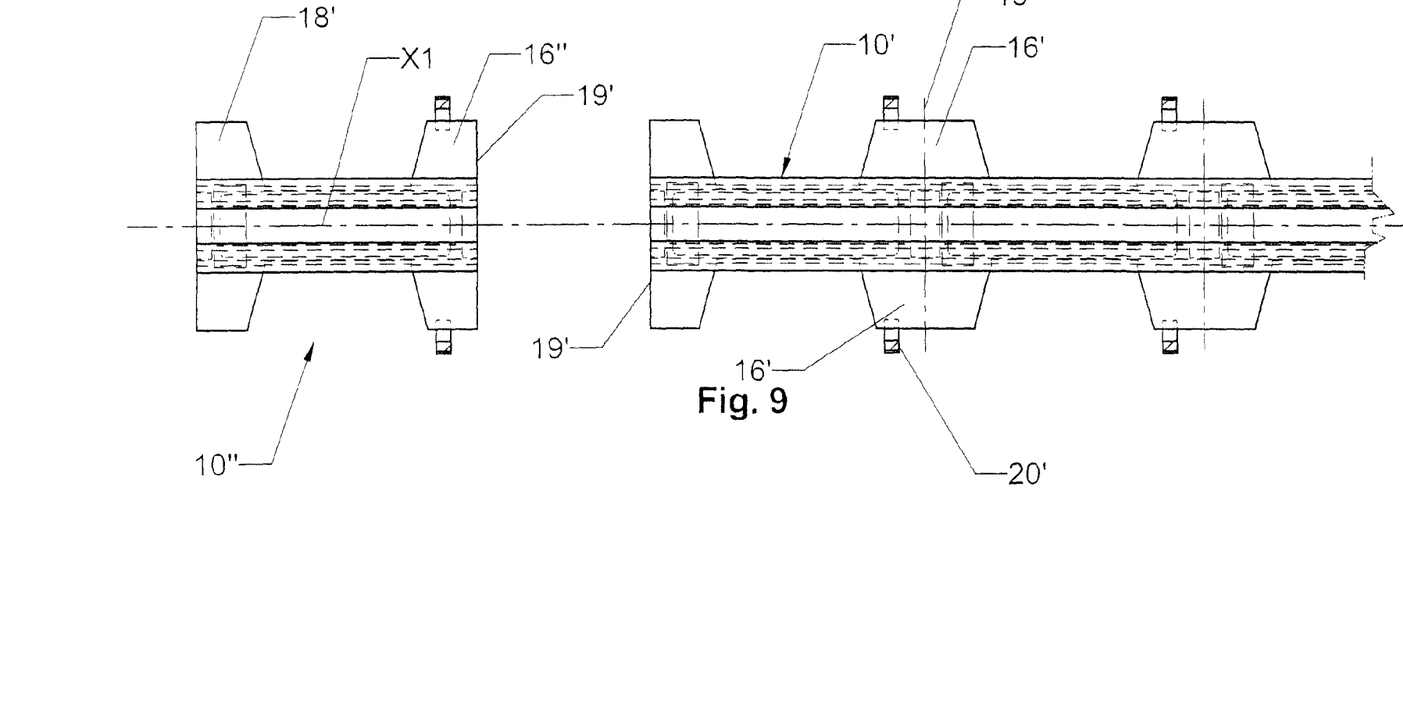

In certain embodiments, as may be appreciated more fully in the views of FIGS. 8 and 9, the aforesaid purpose can be achieved by modifying the shape of the panel 16', specifically lengthening it appropriately, and positioning on each panel the closing system 20', not at the centre of the minor base of the isosceles trapezium, but in the proximity of one of the oblique sides 91'. Obviously, all the other operations will be performed always following the indications described in the present method, up to the moment in which the continuous chain of blanks 10' is subjected to a cutting operation in a direction transverse to the axis X1 along the waistline 19' to form the individual finished products 10".

With the aforesaid transverse cut, also the segmentation of the side panels 16' is performed in such a way as to bestow the characteristic hourglass shape on the sanitary product, where the part of panel that has the closing system 20' on itself remains applied in the rear area of the absorbent product, giving shape to the rear panels 16", whilst the part of panel without closing element 20' comes to form the front panels 18'.

It will likewise be appreciated that in the latter case, after the segmentation of the blanks on the absorbent sanitary product 10", the front and rear panels will have the shape of a right trapezium, with the oblique sides facing the crotch area and the perpendicular side coinciding with the waistline 19'.

It is likewise evident for the person skilled in the branch that the trapezial shape of the panels 16' can be deformed by varying the cutting angles, until the cut 91' becomes perpendicular to the axis X2 so as to have panels of a rectangular shape (it is evident how in this case the square is seen as a particular case of the rectangle).

In the latter configuration, it would likewise be possible to simplify the equipment necessary for implementing the method for production of the diaper described previously; in fact, it is evident that in this particular case it is possible to space the individual panels 16 apart by replacing the cutting unit 90 with a cut-and-slip unit with technical characteristics similar to the ones described previously for the cut-and-slip unit 40, which would enable spacing apart by a constant pitch the individual panels 16 without having to resort to the use of a subsequent repitching unit.

Of course, without prejudice to the principle of the invention, the details of construction and the embodiments may vary, even significantly, with respect to what has been illustrated herein purely by way of non-limiting example, without thereby departing from the scope of the invention as defined by the annexed claims.

The invention claimed is:

1. A method for producing sanitary articles wearable as pants, said articles having a main body including a liquid-impermeable backsheet, a topsheet having a liquid-permeable central sheet and two lateral containment sheets and an absorbing core interposed between the backsheet and the topsheet, said sanitary articles being adapted to be imparted a crotch configuration with end portions arranged at the front and at the back of the wearer, and being provided with at least one pair of side panels to connect said end portions around the wearer's waist, said side panels having a proximal edge for fixing to said main body and a distal edge carrying a closure system to close the sanitary article around the wearer's waistline, the method comprising:
providing a web of a laminar material for said side panels,
cutting said web of a laminar material to produce a segmented chain of said side panels,
connecting the proximal edge of said side panels to a respective lateral containment sheet,
after the connecting step, inverting and spacing the two lateral containment sheets,
after the inverting and spacing step, aligning the two lateral containment sheets by mutually aligning crosswise pairs of side panels, and
after the aligning step, connecting said liquid-impermeable backsheet with the two lateral containment sheets.

2. The method of claim 1, further comprising spacing with a given separation pitch (P2) the side panels in said chain of side panels before connecting the side panels to the respective lateral containment sheet.

3. The method of claim 2, wherein the separation pitch (P2) of said side panels is equal to half the length of the sanitary article.

4. The method of claim 1, further comprising folding the side panels onto the respective lateral containment sheet before inverting and spacing the two lateral containment sheets.

5. The method of claim 1, further comprising joining the side panels to the respective lateral containment sheet via temporary joining spots.

6. The method of claim 5, wherein the temporary joining spots are obtained by at least one of thermo-mechanical welding, ultrasound welding, and application of adhesive.

7. The method of claim 1, wherein connecting the side panels and the respective lateral containment sheet is obtained by at least one of thermo-mechanical welding, ultrasound welding, and application of adhesive.

8. The method of claim 1, wherein the proximal edge of the side panels extend over the corresponding lateral containment sheet by a distance (L) between 5 mm and 25 mm.

9. The method of claim 8, wherein said distance (L) is between 10 mm and 20 mm.

10. The method of claim 1, wherein cutting said web of a laminar material comprises making cuts in a direction which is oblique with respect to the main direction of extension (X2) of the web of laminar material.

* * * * *